(12) United States Patent
Adams

(10) Patent No.: US 6,524,339 B1
(45) Date of Patent: Feb. 25, 2003

(54) CRYOPRESERVED HOMOGRAFTS AND OTHER STENTLESS BIOPROSTHETIC HEART VALVES HAVING NATURAL TISSUE SEWING RINGS

(76) Inventor: David H. Adams, 300 Boylston St., Boston, MA (US) 02116

(*) Notice: Subject to any disclaimer, the term of this patent is extended or adjusted under 35 U.S.C. 154(b) by 0 days.

(21) Appl. No.: 09/238,964

(22) Filed: Jan. 27, 1999

(51) Int. Cl.[7] ................................................ A61F 2/24
(52) U.S. Cl. ....................................................... 623/2.13
(58) Field of Search ........................ 623/2.1, 2.13–2.19, 623/2.36, 2.4, 2.41, 2.42, 918; 606/20

(56) References Cited

U.S. PATENT DOCUMENTS

| | | | |
|---|---|---|---|
| 3,548,418 A | | 12/1970 | Angell et al. |
| 4,629,459 A | | 12/1986 | Ionescu et al. |
| 4,759,759 A | | 7/1988 | Walker et al. |
| 4,890,457 A | * | 1/1990 | McNally ........................ 435/2 |
| 5,156,621 A | * | 10/1992 | Navia et al. ................ 623/2.13 |
| 5,197,979 A | * | 3/1993 | Quintero et al. ............ 623/2.13 |
| 5,336,616 A | | 8/1994 | Livesey et al. |
| 5,352,240 A | | 10/1994 | Ross |
| 5,509,930 A | * | 4/1996 | Love .......................... 623/2.13 |
| 5,593,424 A | | 1/1997 | Northrup, III |
| 5,632,778 A | * | 5/1997 | Goldstein ..................... 623/11 |
| 5,662,704 A | * | 9/1997 | Gross ......................... 623/2.13 |
| 5,713,953 A | | 2/1998 | Vallana et al. |
| 5,733,331 A | * | 3/1998 | Peredo ........................ 623/2.13 |
| 5,769,780 A | * | 6/1998 | Hata et al. .................. 623/2.13 |
| 5,824,063 A | | 10/1998 | Cox |
| 5,824,065 A | | 10/1998 | Gross |
| 5,824,067 A | | 10/1998 | Gross |
| 5,843,180 A | | 12/1998 | Jaffe et al. |
| 5,843,181 A | * | 12/1998 | Jaffe et al. .................. 623/2.13 |
| 5,843,182 A | | 12/1998 | Goldstein |
| 5,910,169 A | * | 6/1999 | Peredo ........................ 623/2.13 |

FOREIGN PATENT DOCUMENTS

| | | |
|---|---|---|
| EP | 0 276 975 A1 | 8/1988 |
| EP | 0 183 904 B1 | 4/1989 |
| EP | 0 402 036 B1 | 5/1990 |
| EP | 0 581 233 B1 | 7/1993 |
| GB | 2 149 062 A | 6/1985 |
| WO | 92/03990 | 3/1992 |
| WO | 93/04643 | 3/1993 |
| WO | 94/07437 | 4/1994 |
| WO | 95/16411 | 6/1995 |
| WO | 95/24873 | 9/1995 |
| WO | 96/07373 | 3/1996 |
| WO | 96/40007 | 12/1996 |
| WO | 96/40012 | 12/1996 |
| WO | 97/00651 | 1/1997 |
| WO | 97/20524 | 6/1997 |
| WO | 97/24082 | 7/1997 |
| WO | 97/24083 | 7/1997 |
| WO | 97/37618 | 10/1997 |

* cited by examiner

Primary Examiner—David H. Willse
Assistant Examiner—Suzette J. Jackson
(74) Attorney, Agent, or Firm—Robert D. Buyan; Stout, Uxa, Buyan & Mullins, LLP

(57) ABSTRACT

Pre-trimmed, cryopreserved homografts and other stentless bioprosthetic heart valves having natural tissue sewing rings formed thereon. The sewing ring may be formed of strip of pericardium or other suitable tissue. Material may be captured between the natural tissue sewing ring and a subvalvular lip formed on the valve to impart a desired size or shape to the sewing ring. In the case of cryopreserved embodiments of the invention (e.g., cryopreserved human homografts) the sewing ring is attached to the valve by way of a natural tissue suture, biological glue or other attachment component that is capable of undergoing cryopreservation without breaking, excessive weakening, or other changes that prevent it from performing its attachment function.

50 Claims, 2 Drawing Sheets

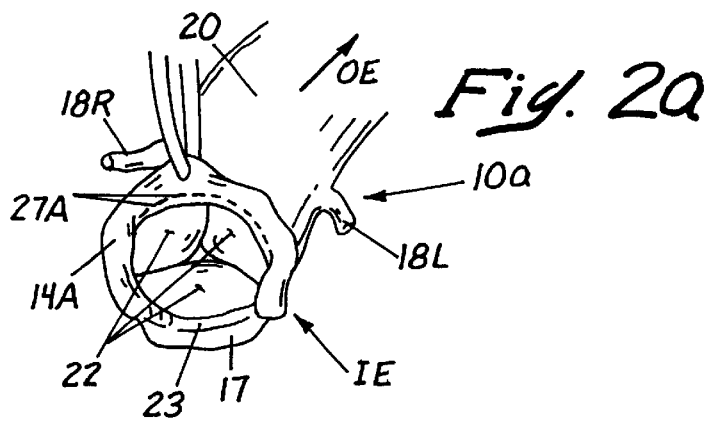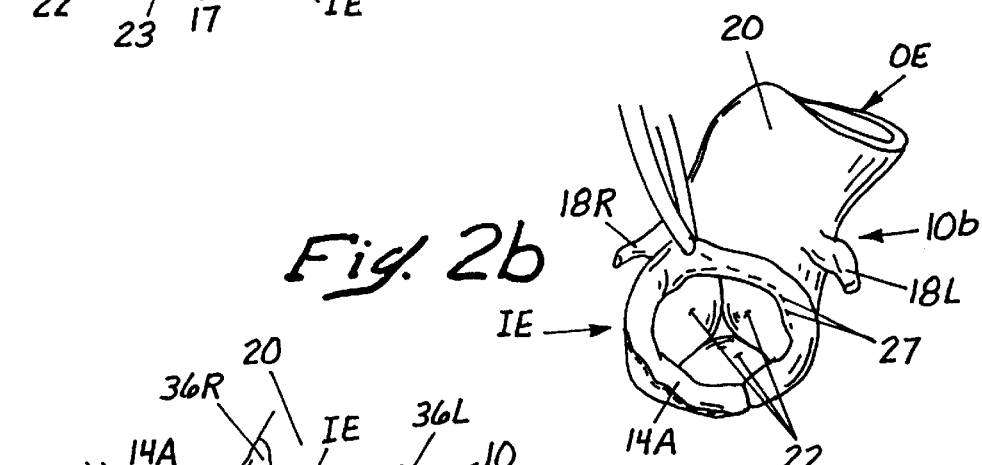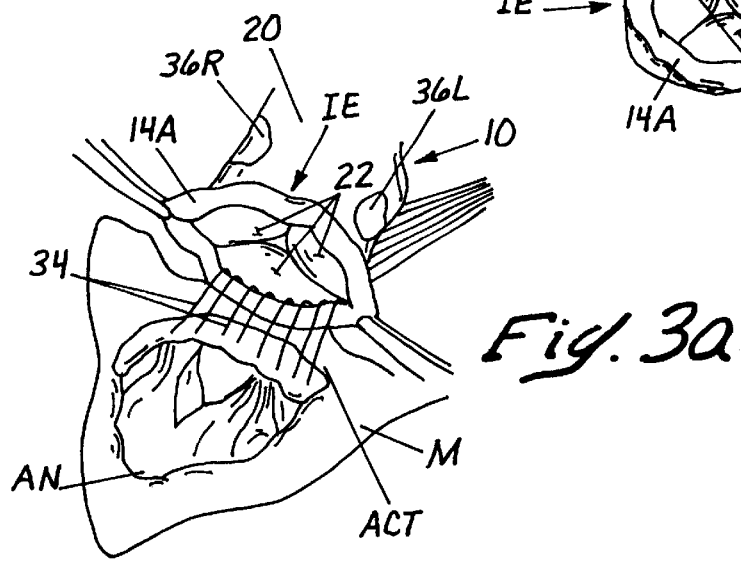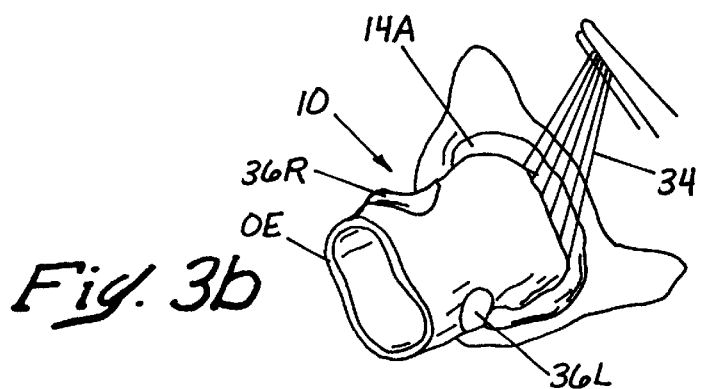

CRYOPRESERVED HOMOGRAFTS AND OTHER STENTLESS BIOPROSTHETIC HEART VALVES HAVING NATURAL TISSUE SEWING RINGS

FIELD OF THE INVENTION

The invention pertains generally to medical method/devices and more particularly to bioprosthetic heart valves, such as cryopreserved, pre-trimmed human homograft valves which have sewing rings formed of natural tissue (e.g., pericardial tissue, dura mater, tendon sheath, etc..) affixed thereto prior to cryopreservation.

BACKGROUND OF THE INVENTION

Heart valve replacement surgeries have been performed in human beings for many years. In these surgeries, a patient's diseased or malfunctioning heart valve is removed and a prosthetic valve is surgically implanted in its place. The available types of prosthetic heart valves include mechanical valves (i.e., valves constructed of non-biological materials such as titanium, carbon or steel) and bioprosthetic valves (i.e., valves formed fully or partially of biological tissue).

A. Bioprosthetic Heart Valves i. Heterografts vs. Homografts

Bioprosthetic valves include heterografts (also known as xenografts) as well as homografts (also known as allografts). Heterograft heart valves are formed of tissue that has been harvested from a non-human animal and subsequently implanted in a human recipient. Homograft heart valves are formed of valvular tissue that has been harvested from the heart of a human being and subsequently implanted in a human recipient.

Typically, heterograft heart valves are formed of tissue that has been harvested from the heart of an animal, such as a pig, and has been treated with a chemical fixative to preserve the tissue for subsequent implantation.

Typically, homograft heart valves are formed of tissue that has been harvested from cadaveric human donors, or from the explanted hearts of human heart transplant recipients whose ailing hearts had healthy valves despite the presence of cardiomyopathy or other cardiac pathology. The harvested homograft tissue is then treated chemically to kill any viruses or other microbes and subsequently cryopreserved (i.e., cooled to a very low temperature by immersion in liquid nitrogen) until the time of implantation. To date, commercially available homograft valves have typically been provided to the surgeon in a non-trimmed state (i.e., with a substantial amount of the donor's muscle tissue (e.g., cardiac septal muscle) affixed to the valve). Thus, prior to implantation, the homograft must be removed from the liquid nitrogen freezer used for the valve bank, thawed by the method recommended by the manufacturer, and then carefully trimmed of excess tissue. This trimming process is laborious and not particularly standardized. Also, this trimming process typically must be performed by a highly trained surgeon.

Stented vs. Unstented

Some bioprosthetic valves, known as "stented" bioprosthetic valves, incorporate a man-made stent or support frame upon which preserved allograft tissue is mounted and an annular sewing ring, formed of man-made materials (e.g., an annular nylon core covered with a knitted polyester sleeve), is formed about the inflow end of the valve to maintain the inflow end of the bioprosthesis in a non-collapsed "open" configuration and to provide a firm suture-holding structure around the valve to facilitate suturing of the valve to the annulus of the recipient. U.S. Pat. No. 4,759,758 (Gabbay) has purported to describe a stented bioprosthetic heart valve formed of a man-made stent having chemically preserved biological tissue (e.g., bovine pericardial tissue), mounted on the man-made stent to form the valve leaflets. Additionally, a quantity of preserved biological tissue or polyester (i.e., Dacron) that has been impregnated with collagen, is mounted about the base of the man-made stent to form a sewing ring thereon.

Examples of commercially available stented bioprosthetic valves include the Carpentier-Edwards®, PERIMOUNT™ Pericardial Bioprosthesis (Baxter Healthcare Corporation, Edwards CVS Division, P.O. Box 11150, Santa Ana, Calif. 92711-1150 as well as the Carpentier-Edwards® Porcine Bioprosthesis (Baxter Healthcare Corporation, Edwards CVC Division, P.O. Box 11150, Santa Ana, Calif. 92711-1150). Each of these valves are of the heterograft type.

Others, known as "stentless" bioprosthetic valves, do not include any manmade stent or support frame, and are formed entirely of preserved biological tissue, and do not include any "sewing rings" formed about their inflow ends.

Examples of commercially available stentless bioprosthetic valves of the heterograft type include the Edwards Prima™ Stentless Bioprosthesis (Baxter Edwards AG, Spierstrasse 5, CH-6848 Horw, Switzerland), the Medtronic Freestyle™ Aortic Root Bioprosthesis (Medtronic, Inc. 7000 Central Avenue NE, Minneapolis, Minn. 55432-3576) and the St. Jude Toronto™ Stentless Bioprosthesis (St. Jude Medical, Inc. One Lillehei Plaza, St Paul, Minn. 55117).

An example of a commercially available stentless bioprosthetic valves of the homograft type is the CryoValve™ cryopreserved aortic homograft (CryoLife Corporation, Atlanta, Ga.).

Stentless bioprosthetic valves may offer superior hemodynamic performance when compared to their stented counterparts, due to the absence of flow restrictions which can be created by the presence of a stent and/or sewing ring. Also, the stentless bioprosthetic valves may exhibit better post-implantation durability than the stented bioprosthetic valves, because they provide a more flexible structure which serves to dissipate stress during the cardiac cycle.

Stentless valves of the homograft type are particularly advantageous in that they exhibit excellent long-term durability and are completely devoid of synthetic or man-made components. The absence of such synthetic or man-made components has been demonstrated to minimize the likelihood of post-operative infection of homograft valves, even in patients who suffer from active endocarditis or other infectious processes within the thoracic cavity. However, the presently available homograft valves are associated with certain drawbacks, namely i) that they require a substantial amount of trimming by the surgeon prior to implantation and ii) the absence of a defined "sewing ring" about the inflow end can cause surgeons to experience difficulty in firmly sewing the inflow end of the homograft valve to the patient's native vale annulus.

B. Methods of Preserving Bioprosthetic Valves

Most bioprosthetic heart valves are formed at least partially of natural tissue that contains high concentrations of connective tissue proteins. Collagen, and to a lesser extent elastin, are the major connective tissue proteins which make-up the connective tissue matrix or framework of most biological tissues. The relative pliability or rigidity of each biological tissue is largely determined by its relative amounts of collagen and elastin and/or by the physical configuration (e.g., structural lattice) and confirmation of the connective tissue matrix.

At present, the natural tissue contained in most bioprosthetic heart valves is preserved, at the time of manufacture, by either chemical fixation (e.g., "tanning") or by cryopreservation (e.g., cooling to a very low temperature by imersion in liquid nitrogen). Each of these tissue preservation techniques has certain advantages and disadvantages, as discussed more fully herebelow.

i. Chemical Fixation

The chemical fixation of biological tissues contained in bioprosthetic heart valves can be accomplished by contacting the tissue with one or more chemicals which will crosslink collagen and elastin molecules which are present within the tissue. Such crosslinking of the collagen and elastin serves to preserve the tissue so that it may be stored until it is needed for implantation in a patient. Examples of the types of biological tissues that are suitable for chemical fixation include cardiac valvular tissue, blood vessels, skin, dura mater, pericardium, ligaments and tendons. These anatomical structures typically contain connective tissue matrices, formed of collagen and elastin, and the cellular parenchyma of each tissue is disposed within and supported by its connective tissue matrix.

Each collagen molecule consists of three (3) polypeptide chains which are intertwined in a coiled helical confirmation. Chemical fixatives (i.e., tanning agents) used to preserve biological tissues generally form chemical cross-linkages between the amino groups on the polypeptide chains within a given collagen molecules, or between adjacent collagen molecules.

Elastin fibers are built by cross-linking (natural linkage) of repeating units of smaller molecules in essentially fibrous strands maintained by rigid cross-linking involving desmosine and isodesmosine. Those chemical fixatives which are used to form cross-linkages between the amino groups of collagen molecules also tend to form such cross-linkages between amino groups of elastin molecules. However, the amount of elastin present in most biological tissues is substantially less than the amount of collagen present therein.

When chemical cross-linkages formed between polypeptide chains within a single collagen or elastin molecule, such cross-linking is termed "intramolecular", while cross-linkages formed between polypeptide chains of different collagen or elastin molecules are termed "intermolecular".

The particular types of chemical fixative agents that have previously been utilized to cross-link collagen and/or elastin in biological tissues include; formaldehyde, glutaraldehyde, dialdehyde starch, hexamethylene diisocyanate and certain polyepoxy compounds.

Glutaraldehyde is the most widely used agent for fixing biological tissues to be as bioprostheses and there are currently a number of commercially available glutaraldehyde-fixed bioprosthetic devices, such as, heart valves of porcine origin having support frames or stents (Carpentier-Edwards® Stented Porcine Bioprosthesis; Baxter Healthcare Corporation; Edwards CVS Division, Irvine, Calif. 92714-5686), prosthetic heart valves formed of a metal frame having leaflets formed of bovine pericardial tissue mounted on said frame (e.g., Carpentier-Edwards®Pericardial Bioprosthesis, Baxter Healthcare Corporation, Edwards CVS Division; Irvine, Calif. 92714-5686) and stentless porcine aortic prostheses (e.g., Edwards® PRIMA™ Stentless Aortic Bioprosthesis, Baxter Edwards AG, Spierstrasse 5, GH6048, Horn, Switzerland).

One problem associated with the implantation of bioprosthetic heart valves that have been preserved by chemical fixation is that they tend to undergo in situ calcification following implantation following implantation. Such calcification can result in undesirable stiffening, degradation and premature failure of the bioprosthesis. Both intrinsic and extrinsic calcification have been known to occur, although the exact mechanism(s) by which such calcification occurs is unknown.

The factors which determine the rate at which chemically-fixed bioprosthetic grafts undergo calcification have not been fully elucidated. However, factors which are thought to influence the rate of calcification include:

a) patient's age;
b) existing metabolic disorders (i.e., hypercalcemia, diabetes, etc.);
c) dietary factors;
d) race;
e) infection;
f) parenteral calcium administration;
g) dehydration;
h) distortion/mechanical factors;
i) inadequate coagulation therapy during initial period following surgical implantation; and
j) host tissue responses.

Glutaraldehyde-fixed bioprosthetic grafts have been observed to calcify sooner than grafts which have been fixed by non-aldehyde fixative agents. Thus, non-aldehyde fixatives, such as polyepoxy compounds (e.g., Denacol Ex-810, Denacol Ex-313) may be useful for manufacturing bioprosthetic graft materials which exhibit improved (i.e., lessened) propensity for calcification.

Other techniques for mitigation calcification of implanted biological tissues are described in U.S. Pat. No. 4,885,005 (Nashef et al.) entitled Surfactant Treatment of Implantable Biological Tissue To Inhibit Calcification; U.S. Pat. No. 4,648,881 (Carpentier et al.) entitled, "Implantable Biological Tissue and Process For Preparation Thereof"; U.S. Pat. No. 4,976,733 (Girardot) entitled, "Prevention of Prosthesis Calcification"; U.S. Pat. No. 4,120,649 (Schechter) entitled, "Transplants"; U.S. Pat. No. 5,002,2566 (Carpentier) entitled, "Calcification Mitigation of Bioprosthetic Implants"; EP 103947A2 (Pollock et al.) entitled, "Method For Inhibiting Mineralization of Natural Tissue During Implantation" and WO84/01879 (Nashef et al.) entitled, "Surfactant Treatment of Implantable Biological Tissue to Inhibit Calcification"; and, in Yi, D., Liu, W., Yang, J., Wang, B., Dong, G., and Tan, H.; *Study of Calcification Mechanism and Anti-calcification On Cardiac Bioprostheses* Pgs. 17–22, Proceedings of Chinese Tissue Valve Conference, Beijing, China, June 1995.

The overall biocompatability (e.g., antigenicity and immunogenicity) of the fixed graft material can significantly affect the severity of post-implantation graft calcification, and may also be a factor in the occurrence of other undesirable sequelae such as platelet activation, thrombogenesis, local inflammation, and/or graft failure.

iii. Cryopreservation

Cryopreservation is a tissue preservation technique wherein the tissue is cooled to an extremely low temperature and maintained in a frozen state. This cryopreservation of the tissue is typically accomplished by placing the tissue in a bath solution containing certain cryoprotectants (i.e., chemicals that protect the tissue from damage or degradation during freezing) and immersing it in liquid nitrogen to effect rapid and extreme cooling of the tissue and bath solution. The tissue then remains in the liquid nitrogen until it is desired to implant the tissue. At that time, the tissue is removed from the liquid nitrogen and thawed. Examples of specific cryopreservation techniques that have heretofore been used with homograft heart valves are described in U.S. Pat. No. 4,890,457 (McNally, et al) and U.S. Pat. No. 5,632,778 (Goldstein), the entire disclosures of which are expressly hereby incorporated by reference.

SUMMARY OF THE INVENTION

The present invention overcomes shortcomings of prior cryopreserved homograft heart valves by providing a pre-trimmed, specifically sized, cryopreserved homograft that has a sewing ring formed of cryopreservable natural tissue (e.g, pericardium) affixed at least partially about the inflow end of the homograft. Marking(s) may be formed on the natural tissue sewing ring to indicate a location(s) through which sutures may be passed to ensure that such sutures will engage (i.e., pass through) underlying annular connective tissue of the homograft.

Additionally, the present invention overcomes certain shortcomings of chemically fixed stentless heart valve bioprostheses of the prior art by providing a stentless bioprosthesis that has a sewing ring formed of natural tissue (e.g., pericardium) formed at least partially about the inflow end of the bioprosthesis. Such natural tissue sewing ring is less likely to become infected that other types of sewing rings made fully or partially of man-made materials such as polyester mesh.

Further aspects and objects of the present invention will become apparent to those of skill in the relevant art upon reading and understanding of the following detailed description of certain preferred embodiments and examples, and the drawings to which it refers.

BRIEF DESCRIPTION OF THE DRAWINGS

FIG. 2a is a perspective view of an aortic homograft of the present invention having a natural tissue sewing ring that extends 270 degrees about the inflow end of the bioprosthesis.

FIG. 2b is a perspective view of another aoritc homograft of the present invention having a natural tissue sewing ring that extends 360 degrees about the inflow end of the bioprosthesis.

FIGS. 3a and 3b are showings of a preferred method of passing sutures through the natural tissue sewing ring of an aortic homograft to attach the inflow end of the homograft to the native aortic annulus of the recipient patient.

DETAILED DESCRIPTION OF PREFERRED EMBODIMENT

The following detailed description, and the figures to which it refers, are provided for the purpose of describing example(s) and specific embodiment(s) of the invention only and are not intended to exhaustively describe all possible examples and embodiments of the invention.

Figure 1A:
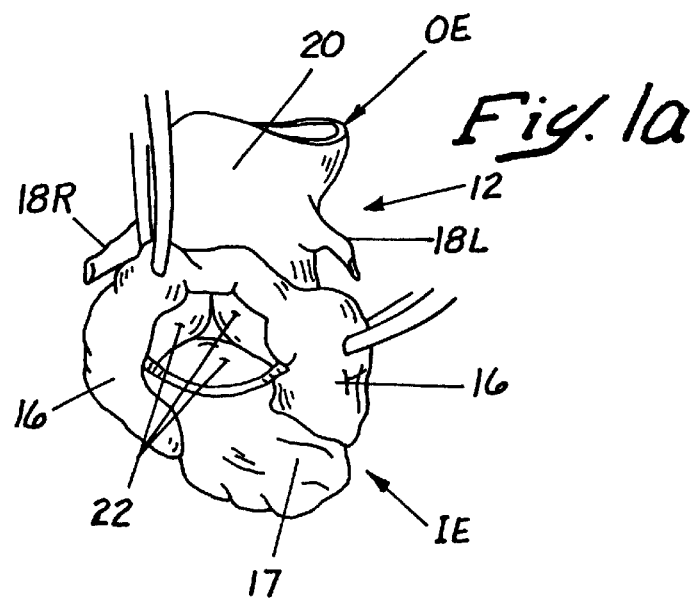
FIGS. 1a–1c are step-by-step showings of a preferred method for mounting a natural tissue sewing ring about the inflow end of an aortic homograft.
Figure 1B:
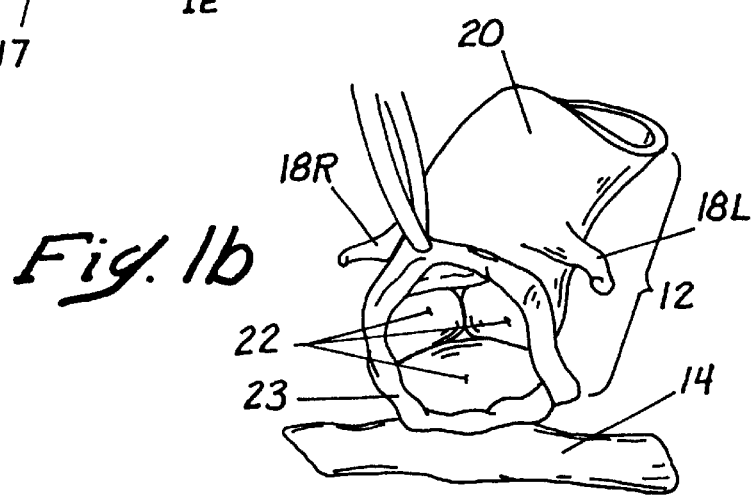
Figure 1C:
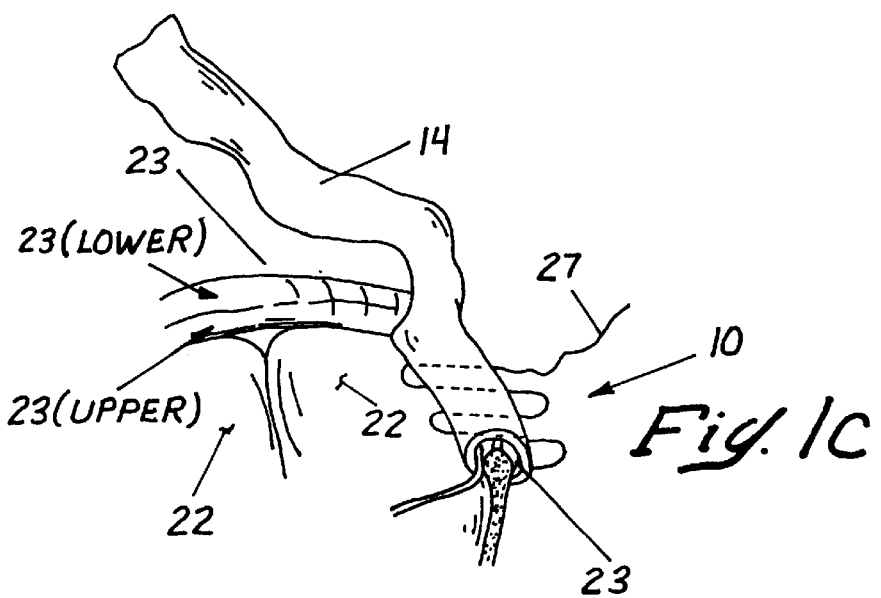

A. Harvesting, Assembly and Preparation of an Aortic Homograft of the Present Invention FIGS. 1a–1c show, in step-by-step fashion, a preferred method for constructing an aortic homograft 10 of the present invention.

ii. Harvesting and Pre-Trimming of Aortic Segment

As shown, a segment of ascending aorta 20 having remnants of the right and left coronary arteries 18R, 18L extending therefrom and the leaflets 22 of the donor's aortic valve positioned therewithin is excised and harvested from the heart of a human donor. Typically, a quantity of muscle 16 and fiberous connective tissue of one mitral valve leaflet 17 will remain attached to the inflow end IE of the harvested aortic segment 20. Such muscle 16 and fiberous connective tissue 17 is subsequently trimmed to form a subvalvular tissue lip 23 that extends about the inflow end IE, beneath the valve leaflets 22. As indicated in FIG. 1c, the upper portion of this subvalvular tissue lip $23_{(upper)}$ is formed of annular connective tissue and the lower portion of this subvalvular lip $23_{(lower)}$ is formed of muscle tissue. This subvalvular tissue lip 23 is typically 3–4 mm in length.

ii. Harvesting of Sewing Ring Tissue Strip

A generally rectangular tissue strip 14 is harvested from a donor and such tissue strip 14 is then used to form the natural tissue sewing ring 14A. The tissue strip 14 preferably comprises pericardial tissue that has been harvested from the same donor as the aortic segment 20. However, it will be appreciated that other types of relatively durable tissue may also be useable to form the sewing ring 14A. Examples of other types of tissue that may be used include dura mater, plantar fascia or the sheaths of tendons. It will be further appreciated that the tissue strip 14 could be harvested from a human donor other than the donor from whom the aortic segment was harvested (e.g., from the recipient into whom the homograft is to be implanted or another human donor) or from another animal species (e.g., porcine, bovine, etc.). The tissue strip 14 is trimmed to a size that is suitable to fit upon the inflow end IE of the aortic segment 20 as shown in FIG. 1c.

iii. Attaching the Sewing Ring Tissue Strip to the Aortic Segment

As shown in FIG. 1c, the tissue strip 14 is curled over or wrapped partially around the subvalvular tissue lip 23 in a generally unshaped configuration, and suture material 27 is passed through both sides of the tissue strip 14 at or slightly above the junction of the upper and lower portions $23_{(upper)}$, $23_{(lower)}$ of the lip 23, to form a continuous suture line 27A. This suture line 27A secures the tissue strip 14 to the inflow end IE if the aortic segment 20, thus forming the natural tissue sewing ring 14A. The suture line 27A may be formed of a colored or readily visible suture material to clearly delineate the boundary between the upper and lower portions $23_{(upper)}$, $23_{(lower)}$ of the tissue lip 23, such that subsequent placement of sutures above this suture line 27a will ensure that those subsequent sutures will pass through the relatively strong annular connective tissue of the tissue lip's upper portion $23_{(upper)}$ rather than through the muscle tissue of the tissue lip's lower portion $23_{(lower)}$. Optionally, a second suture line (not shown) may be placed above suture line 27A in substantial parallel therewith, but below the valve leaflets 22. Such second suture line (not shown) will thus denote a zone (i.e., a region between the lower suture line 27A and the second suture line formed thereabove but not shown on the drawings) through which subsequent sutures may be passed with assurance that those subsequent sutures will a) pass through the relatively strong annular connective tissue of the tissue lip's upper portion $23_{(upper)}$ rather than through the muscle tissue of the tissue lip's lower portion $23_{(lower)}$ and b) not injure or impair the valve leaflets 22.

In some cases, the tissue strip 14 will be attached such that it extends approximately 270 degrees around the inflow end IE of the aortic segment 20 while, in other cases, the tissue strip 14 will be attached such that it extends fully 360 degrees around the inflow end IE of the aortic segment 20.

In some cases a quantity of additional material or fabric (not shown) such as additional layers of sewing ring tissue strip 14, a mass of biological matter such as a biological glue, fibrin glue, collagenous material, gelatinous material, polyester mesh, nylon, felt, or other material may be positioned and captured between the tissue lip 23 and the tissue strip 14. This may serve to impart additional bulk or a specific shape (e.g., an oval, oblong or crescent shape) to the sewing ring 14A. The desirability of imparting a slightly oblong, oval or crescent shape to the sewing ring 14A is explained in more detail herebelow in connection with the surgical implantation of the homograft 10.

It will be appreciated that, where the homograft is to be cryopreserved, the sewing ring tissue strip 14, any additional tissue or bulking material, and the suture material 27 used to attach the sewing ring tissue strip 14 to the tissue lip 23 must be formed of material that is capable of being frozen at extremely low cryopreservation temperatures without degrading, crumbling, breaking or otherwise losing the ability to firmly affix the sewing ring 14A in its desired position on the homograft 10. For this reason, it is desirable that the suture material 27 be of a cryopreservable natural (or synthetic) material (e.g., cat gut or metal wire) or a "suture" crafted from a narrow strip of relatively strong donor tissue such as dura mater, pericardium or fascia. In this regard, as an alternative to or in addition to, the suture line 27A a cryopreservable adhesive material may be used to affix the sewing ring 14A to the tissue lip 23 of the aortic segment 20. For example, a biological adhesive such as a fibrin glue may withstand the extremely low temperature of cryopreservation and would thus be sufficiently cryopreservable and suitable for this purpose.

The fabrication of this sewing ring 14A on the inflow end IE of the aortic segment 20 completes the initial fabrication of the aortic homograft 10.

iv. Bioburden Reduction or Sterilization

Prior to, during and/or after the initial fabrication of the homograft 10 has been completed, the homograft 10 and/or the components thereof may be immersed one or more times in a suitable microbicidal or antibiotic solution to reduce any microbial or bacterial content of the tissue. Alternatively or additionally, the homograft 10 may be sterilized by any sterilization technique that is suitable for such homograft tissue.

V. Cryopreservation

After the homograft 10 has been sterilized, it is subjected to a suitable cryopreservation process, examples of which are described in U.S. Pat. No. 4,890,437 (McNally, et al) and U.S. Pat. No. 5,632,778 (Goldstein), the entire disclosures of which are expressly hereby incorporated by reference. At the time of cryopreservation, the homograft 10 may be placed in a sealed in a pouch or container that has been filled with a storage solution containing certain cryoprotectants (e.g., substances which when added during the freezing of tissue or cells help to prevent freezing damage).

Although cryopreservation is believed to be the preferred method for preservation of homografts 10 of this type, it will be appreciated that other tissue preservation techniques, such as the chemical fixation or "tanning" techniques described hereabove, may be used to preserve the entire homograft 10 or portions thereof such as the sewing ring tissue strip 14.

B. Surgical Replacement of a Malfunctioning Aortic Valve Using an Aortic Homograft of the Present Invention FIGS. 3a and 3b illustrate one aspect of the preferred methods for surgical implantation of a pre-trimmed, cryopreserved, sewing ring-equipped aortic homograft 10 of the present invention. Detailed descriptions of alternative procedures for implanting this homograft 10 are set forth herebelow. The procedural descriptions serve to illustrate certain advantages of this pre-trimmed, sewing-ring equipped homograft 10 of the present invention over the prior art aortic homografts.

Initially, the pre-trimmed, sewing-ring equipped aortic homograft 10 is thawed and removed from its protective pouch. In contrast to aortic homografts of the prior art, no trimming of this homograft 10 is required after thawing, as excess septal muscle tissue has previously been trimmed away prior to attachment of the natural tissue sewing ring and prior to cryopreservation.

The patient is anesthetized and an incision is made in the chest to gain access to the patient's heart. In most cases, either a) a midline sternotomy incision or b) a minimal approach using a lower ½ sternotomy incision, is used. The patient is then placed on cardiopulmonary bypass using a single venous cannula (two stage) with oxygenated blood return provided to the ascending aorta. In cases where substantial infection of the aortic root is present, two venous cannulae may be used to allow for entry through the right atrium or ventricle if such entry should be deemed necessary during the procedure. A vent catheter is inserted through the right superior pulmonary vein and into the left atrium and left ventricle.

The ascending aorta is then occluded at the pericardial reflection and a flow of hypothermic cardioplegia solution is administered to the heart to assure total electro mechanical arrest and to protect the myocardium from ischemic injury during the procedure. The cardioplegia solution is preferably retro-perfused through the coronary veins, by way of a catheter that has been inserted into the coronary sinus. This type of retrograde venous perfusion is preferred over antegrade arterial perfusion because it can be fully effective even in patients who suffer from severe aortic valve incompetence and, additionally, because it avoids the need for placing any perfusion cannula in the aortic root.

Thereafter, the endogenous aortic valve is removed and the homograft 10 is implanted in its place, by one of several possible techniques, including a) complete aortic root replacement techniques wherein the entire aortic root including the aorto-coronary junctions are replaced by the homograft 10 and b) sub-coronary techniques wherein only the portion of the homograft proximal to the coronary ostia is implanted (leaving the recipient patient's existing aorto-coronary anatomy in tact). Examples of a complete aortic root replacement technique and a subcoronary technique are described in significant detail herebelow, with reference to the showings of FIGS. 2a–3b. It is to be appreciated, however, that these descriptions are merely examples of possible implantation techniques and numerous other techniques or modifications thereof may also be used.

i. Complete Aortic Root Homograft Technique

In the complete aortic root technique, the ascending aorta is divided above the sinotubular junction. The sinus aorta surrounding the coronary arteries is retained such that "buttons" of tissue surround the free end of each of the left and right main coronary arteries. The remainder of the sinus aorta is excised leaving only fibrous aortic valve attachments which are normal and uninvolved with the disease process which is being treated.

The diameter of the aortic root at the level of valve cusp attachment (annulus) is determined using standard sizing devices. An appropriately sized aortic homograft 10 of the present invention is selected for implantation. Sizing of the homograft 10 to be used in this complete aortic root replacement is of less importance than in a freehand valve replacement because the homograft 10 will not be enclosed by host aorta. Nonetheless, it is desirable for the internal diameter of the selected homograft may be slightly (e.g., 1–2 mm) smaller than the measured diameter of the aortic annulus. Such down-sizing of the aortic homograft can allow for minor post-operative shrinkage of the graft cusp tissues and for absorption of the septal myocardium. However, too much downsizing of the aortic homograft can result in aortic valve incompetence 3 or 4 months after operation. The presence of the natural tissue sewing ring 14A formed about the inflow end IE of the homograft 10 facilitates firm suturing of the slightly undersized homograft 10 to the annular connective tissue ACT surrounding the homograft 10 without tearing through of the sutures as can occur with the homografts of the prior art that do not include such sewing ring 14A. Thus, the presence of the sewing ring 14A serves to facilitate such purposeful undersizing of the cusp of the homograft 10.

A proximal suture line attaching the homograft 10 to the left ventricular outflow tract is begun by placing simple interrupted or mattress stitches 34 of appropriate suture material (e.g., 4/0 Ethibond braided suture material) through the annular connective tissue ACT surrounding the patient's valve annulus AN, as shown in FIG. 3A. In cases where the annular connective tissue ACT has been removed or destroyed by the disease process, these stitches 34 may be placed through septal myocardium and the unsupported anterior leaflet of the mitral valve and/or roof of left atrium to gain sufficient suture-holding capacity in the absence of sufficient annular connective tissue ACT.

After the sutures 34 have been passed through the patient's annular connective tissue ACT, they are similarly passed through the natural tissue sewing ring 14A at a location whereby they pass through the annular connective tissue of the upper portion of the homograft's subvalvular tissue lip $23_{(upper)}$ located between the opposite sides of the pericardial tissue strip 14. In instances where the suture line 27A has been located at or slightly above the junction of the upper and lower tissue lip portions $23_{(upper)}$, $23_{(lower)}$ such suture line 27A may be used as a guide and the surgeon may place these sutures 34 just above that suture line 27A thereby ensuring that these sutures 34 will pass through the relatively strong connective tissue of the homograft's upper tissue lip $23_{(upper)}$. Where a second, parallel suture line (not shown) has also been provided, as described hereabove, the surgeon may place these sutures 34 above the lower suture line 27A but below the upper parallel suture line (not shown), thereby ensuring that the sutures 34 so placed will pass a) through the relatively strong connective tissue of the homograft's upper tissue lip $23_{(upper)}$ but b) below the valve leaflets 22 so as not to interfere with, injure or impair the valve leaflets.

In the past, some surgeons have elected to place a reinforcing collar, formed of a strip of polytetrafluoroethylene (i.e., Teflon) felt material or a cut segment of the recipient's pericardium approximately 5 mm wide, between the inflow end of a homograft (without a sewing ring) and the surrounding tissue of the recipient's annulus AN to ensure a hemostatic proximal suture line and to prevent excessive dilation of the root of the aortic homograft 10.

The homograft is then downwardly slipped over the sutures 34 until the natural tissue sewing ring 14A of the homograft 10 is in firm abuttment with the annular connective tissue ACT (or other tissue) surrounding the host annulus AN. The sutures 34 are then tied down. The strength and tear resistance of the natural tissue sewing ring 14A allows the surgeon to firmly tie these sutures 34 to effectively prevent leakage at the proximal suture line formed thereby.

The coronary ostia of the graft are enlarged to create openings 36R and 36L that are sized to receive the "buttons" of tissue formed on the ends of the host coronary arteries. These coronary buttons are then anastomosed to the homograft tissue surrounding these openings 36R, 36L using continuous stitches of 4/0 or 5/0 polypropylene suture.

The repair is completed by end-to-end anastomosis of the outflow end OE of the homograft 10 to the patient aorta. Continuous stitches of 4/0 polypropylene are used to form this distal anastomosis.

ii. Subcoronary Aortic Homograft Technique

In this subcoronary technique, only the portion of the homograft proximal to the coronary ostia is implanted. The remaining distal portion of the homograft's aortic segment 14, including the coronary artery remnants 18R, 18L, are cut away and discarded.

The ascending aorta is divided above the sinotubular junction. This provides optimal exposure while retaining the natural relationships of the aortic root. The aortic valve is excised and the annular connective tissue ACT surrounding the annulus AN and sinus aorta are debrided of any calcium deposits. The diameter of the aortic root at the level of valve cusp attachment (annulus) is determined using a sizing device of the type well known in the art and an appropriately sized homograft 10 of the present invention is selected by the surgeon as described hereabove with respect to the full root procedure.

The sinus aorta is trimmed away from the valve cusps leaving a 3–4 mm rim of aorta beyond the attachment of the cusps. Most of the sinus aorta will be removed from the right and left coronary sinuses. The noncoronary sinus aorta remains intact in order to fix the position of the two adjacent commissures. The aorta is shortened to approximately the same distance above the top of the commissural attachment between the left and right sinuses.

Three stitches may be used to attach the homograft 10 to the outflow tract. For example, the first stitch may be of an appropriate material (e.g., 3/0 polypropylene) with two small strong needles (RB-1). A monofilament suture of this type may be chosen due to its needle strength and because the suture loops slide easily without tendency to cut through the homograft 10 tissue. This suture is passed through the graft septal muscle below the appropriate commissure and then through the host aortic outflow tract below the medial commissure between the right and left coronary sinuses. This first stitch is placed below the annulus of the host aortic valve. Thereafter, two alignment sutures are placed to ensure alignment of the homograft to the aortic root. These alignment stitches are formed of appropriate suture material (e.g., 4/0 polypropylene) and are subsequently removed as the primary suture line comes to involve their position. These stitches are placed beneath the appropriate commissure of the graft, directly below the anterior and posterior commissures of the host aorta.

The homograft 10 is then advanced into position on the aortic root while being guided by the alignment sutures. The commissures of the graft are inverted through its annulus AN into the left ventricle of the host, thereby exposing the natural tissue sewing ring 14A on the inflow end IE of the homograft 10. A knot is placed in the primary suture and the stay sutures are pulled taught to bring the homograft into alignment with the aortic outflow tract.

A proximal anastomosis is formed by passing sutures 34 are passed through the natural tissue sewing ring 14A and the annular connective tissue ACT. The patient's aortic annulus AN is usually not truly annular but rather somewhat oblong or crescent shaped. Thus, the stitches 34 may actually be placed below the fibrous "annulus" AN and in the sub-commissural region or interleaflet triangle and will come through this fibrous tissue at the mid-point of the aortic sinus. Alternatively, it will be appreciated that the natural tissue sewing ring 14A may be built-up in selected regions by the presence of additional layers of sewing ring tissue (e.g., pericardium) or an other cryopreservable bulking material (e.g., biological glue, fibrin glue, other tissue, etc) to cause the sewing ring to have an oblong, oval or somewhat crescent shape so as to more precisely match with the native annulus AN.

The commissures of the aortic homograft 10 are then pulled out of the left ventricle so that the valve leaflets 22 assume a normal position and configuration. The sinus aorta of the homograft 10 is the anastomosed to the host aorta by continuous suture using an appropriate suture material such as 4/0 polypropylene. Separate stitches are used for the right and left aortic sinuses, and such stitches are positioned below the coronary ostia, in the sinus of Valsalva. As the suturing proceeds up the commissure, the stitches in the host aorta are preferably placed away from the actual fibrous commissure in the tissue of the aortic sinus so as to cause homograft commissure to be flat against the host aortic wall. The final stitches securely fasten the commissure of the homograft 10 to the aortic wall.

The placement of these distal sutures continues in each aortic sinus until the homograft 10 has been completely attached. Generally, the right coronary sinus is completed first, sewing from the center point of the sinus to each of the commissures using opposite ends of the suture. The left sinus is then sewn in a similar manner. The noncoronary sinus aorta of the aortic segment 14 of the homograft 10 is trimmed so as to be flush with the cut edge of the aorta so that the two edges may be approximated and joined simply by over and over continuous suturing.

The repair is then completed by anastomosis of the ascending aorta to the aortic root, the patient is removed from cardiopulmonary bypass, and the thoracotomy (sternotomy) incision is closed.

It will be appreciated that the invention has been described hereabove with reference to certain examples or preferred embodiments as shown in the drawings. Various additions, deletions, changes and alterations may be made to the above-described embodiments and examples without departing from the intended spirit and scope of this invention. For example, the homograft need not be formed of aortic tissue but, rather, may be formed on the donor's pulmonary valve and adjacent segment of pulmonary artery (i.e., a pulmonary homograft). Also, the sewing ring tissue strip 14 used to form the natural tissue sewing ring 14A need not necessarily be made of cryopreserved tissue harvested from the same donor as the valve itself, but rather may be a chemically fixed ("tanned") instead of cryopreserved and/or may have been harvested from any suitable human or animal (e.g., porcine, bovine) donor. Additionally, this invention includes cryopreserved stented or stentless heterografts formed wholly or partially of tissues that have been harvested from non-human animal species (e.g., porcine, bovine), such as pigs that have been genetically altered or genetically engineered to produce tissue that is human-compatable and can be transplanted into human recipients without rejection or significant immunogenic reaction. Accordingly, it is intended that all such additions, deletions, changes and alterations be included within the scope of the following claims.

What is claimed is:

1. A cryopreserved heart valve homograft comprising:
    a generally tubular segment of vascular tissue harvested from a mammalian donor, said tubular segment having an inflow end and an outflow end and a plurality of valve leaflets disposed within said tubular segment a spaced distance above the inflow end, the inflow end of said tubular segment being trimmed to form a subvalvular lip; and,
    a sewing ring formed of tissue harvested from a human donor, said sewing ring being attached by a cryopreservable attachment component to said subvalvular lip;
    said tubular segment having said sewing ring attached thereto being cryopreserved.

2. A homograft according to claim 1 wherein the sewing ring comprises pericardium.

3. A homograft according to claim 1 wherein said generally tubular segment comprises a segment of the donor's aorta and said leaflets comprise the donors aortic valve leaflets.

4. A homograft according to claim 1 wherein said generally tubular segment comprises a segment of the donors pulmonary artery and said leaflets comprise the donor's pulmonary valve leaflets.

5. A homograft according to claim 1 wherein the cryopreservable attachment component is selected from the group consisting of:
    a cryopreservable suture material;
    catgut suture material;
    suture material prepared from natural tissue;
    a cryopreservable adhesive;
    a biological adhesive;
    a fibrin glue;
    possible combinations thereof.

6. A homograft according to claim 1 wherein the sewing ring comprises a tissue that is selected from the group of tissues consisting of:
    pericardium;
    dura mater;
    tendon sheath;
    fascia; and,
    possible combinations thereof.

7. A homograft according to claim 1 wherein the sewing ring further comprises cryopreservable material that is captured between the subvalvular lip and said sewing ring tissue.

8. A homograft according to claim 7 wherein the cryopreservable material captured between the subvalvular lip and said sewing ring tissue is located to impart a desired shape to said sewing ring.

9. A homograft according to claim 1 wherein the subvalvular lip has an upper portion formed substantially of connective tissue and a lower portion formed substantially of other than connective tissue, and wherein the homograft further comprises marking formed on the sewing ring to denote the location of said upper portion of the subvalvular lip.

10. A homograft according to claim 1 wherein the subvalvular lip has been trimmed to provide a sewing ring of predetermined length and diameter.

11. A cryopreserved stentless heart valve bioprosthesis comprising:

a generally tubular segment of vascular tissue that has an inflow end and an outflow end;

a plurality of valve leaflets disposed within said tubular segment a spaced distance above the inflow end such that a subvalvular lip exists at the inflow end of the tubular segment beneath the valve leaflets;

a sewing ring that has been attached to and extends at least partially about the subvalvular lip of said tubular segment, said sewing ring comprising sewing ring tissue that has been harvested from a mammalian donor; and a cryopreservable attachment component attaching the sewing ring to said subvalvular lip.

12. A stentless heart valve bioprosthesis according to claim 11 wherein the sewing ring comprises a strip of pericardium that has been attached to the subvalvular lip of the generally tubular segment.

13. A stentless aortic valve bioprosthesis according to claim 11 wherein said generally tubular segment comprises a segment of the donor's aorta and said leaflets comprise the donor's aortic valve leaflets.

14. A stentless pulmonary valve bioprosthesis according to claim 11 wherein said generally tubular segment comprises a segment of the donor's pulmonary artery and said leaflets comprise the donors pulmonary valve leaflets.

15. A stentless heart valve bioprosthesis according to claim 11 wherein at least the tubular segment and the leaflets were harvested from a donor of the same species as the recipient into whom the stentless heart valve homograft is to be implanted.

16. A stentless heart valve bioprosthesis according to claim 11 wherein the sewing ring comprises tissue that was harvested from a donor of the same species as the recipient into whom the stentless heart valve homograft is to be implanted.

17. A stentless heart valve bioprosthesis according to claim 11 wherein the sewing ring comprises a tissue that is selected from the group of tissues consisting of:

pericardium;
dura mater;
tendon sheath;
fascia; and,
possible combinations thereof.

18. A stentless heart valve bioprosthesis according to claim 11 formed entirely of biological tissue that is cryopreservable.

19. A stentless heart valve bioprosthesis according to claim 18 wherein the cryopreservable attachment component is selected from the group consisting of:

a cryopreservable suture material;
suture material prepared from natural tissue;
a cryopreservable adhesive;
a biological adhesive;
a fibrin glue;
possible combinations thereof.

20. A stentless heart valve bioprosthesis according to claim 11 wherein the biological tissue thereof is preserved by chemical fixation.

21. A stentless heart valve bioprosthesis according to claim 11 wherein the sewing ring further comprises a quantity of material that is captured between the subvalvular lip and said sewing ring tissue.

22. A stentless heart valve bioprosthesis according to claim 21 wherein the material captured between the subvalvular lip and said sewing ring tissue is sized and located to impart a desired shape to said sewing ring.

23. A stentless heart valve prosthesis according to claim 11 formed entirely of cryopreservable material.

24. A stentless heart valve prosthesis according to claim 23 which has been cryopreserved.

25. A stentless heart valve prosthesis according to claim 24 wherein the bioprosthesis is a heterograft formed of tissue harvested from a non-human species.

26. A stentless heart valve prosthesis according to claim 25 wherein the animal from which the tissue is harvested was genetically engineered to produce tissue suitable for transplantation into a human recipient without substantial immunogenic rejection.

27. A cryopreserved heart valve homograft comprising:

a generally tubular segment of vascular tissue harvested from a mammalian donor, said tubular segment having an inflow end and an outflow end and a plurality of valve leaflets disposed within said tubular segment a spaced distance above the inflow end, the inflow end of said tubular segment being trimmed to form a subvalvular lip;

a sewing ring formed of tissue harvested from a human donor; and a cryopreservable attachment component attaching the sewing ring to said subvalvular lip, said cryopreservable attachment component been selected from the group consisting of:
a cryopreservable suture material; and
a cryopreservable adhesive, said tubular segment having said sewing ring attached thereto using said cryopreservable attachment component been cryopreserved.

28. A homograft according to claim 27 wherein the sewing ring comprises pericardium.

29. A homograft according to claim 27 wherein the sewing ring comprises a tissue that is selected from the group of tissues consisting of:

dura mater;
tendon sheath;
fascia; and,
possible combinations thereof.

30. A homograft according to claim 27 wherein said generally tubular segment comprises a segment of the donor's aorta and said leaflets comprise the donor's aortic valve leaflets.

31. A homograft according to claim 27 wherein said generally tubular segment comprises a segment of the donor's pulmonary artery and said leaflets comprise the donor's pulmonary valve leaflets.

32. A homograft according to claim 27 wherein the sewing ring further comprises cryopreservable material that is captured between the subvalvular lip and said sewing ring tissue.

33. A homograft according to claim 32 wherein the cryopreservable material captured between the subvalvular lip and said sewing ring tissue is located to impart a desired shape to said sewing ring.

34. A homograft according to claim 27 wherein the subvalvular lip has an upper portion formed substantially of connective tissue and a lower portion formed substantially of other than connective tissue, and wherein the homograft further comprises marking formed on the sewing ring to denote the location of said upper portion of the subvalvular lip.

35. A homograft according to claim 27 wherein the subvalvular lip has been trimmed to provide a sewing ring of predetermined length and diameter.

36. A stentless heart valve bioprosthesis comprising:

a generally tubular segment of vascular tissue that has an inflow end and an outflow end;

a plurality of valve leaflets disposed within said tubular segment a spaced distance above the inflow end such that a subvalvular lip exists at the inflow end of the tubular segment beneath the valve leaflets;

a sewing ring that has been attached to and extends at least partially about the subvalvular lip of said tubular segment, said sewing ring comprising sewing ring tissue that has been harvested from a mammalian donor; and, a cryopreservable attachment component attaching the sewing ring to said subvalvular lip selected from the group consisting of:

a cryopreservable suture material; and a cryopreservable adhesive.

37. A stentless heart valve bioprosthesis according to claim 36 wherein the sewing ring comprises a strip of pericardium that has been attached to the subvalvular lip of the generally tubular segment.

38. A stentless heart valve bioprosthesis according to claim 36 wherein the sewing ring comprises a tissue that is selected from the group of tissues consisting of:

dura mater;

tendon sheath;

fascia; and, possible combinations thereof.

39. A stentless aortic valve bioprosthesis according to claim 36 wherein said generally tubular segment comprises a segment of the donor's aorta and said leaflets comprise the donor's aortic valve leaflets.

40. A stentless pulmonary valve bioprosthesis according to claim 36 wherein said generally tubular segment comprises a segment of the donor's pulmonary artery and said leaflets comprise the donor's pulmonary valve leaflets.

41. A stentless heart valve bioprosthesis according to claim 36 wherein at least the tubular segment and the leaflets were harvested from a donor of the same species as the recipient into whom the stentless heart valve homograft is to be implanted.

42. A stentless heart valve bioprosthesis according to claim 36 wherein the sewing ring comprises tissue that was harvested from a donor of the same species as the recipient into whom the stentless heart valve homograft is to be implanted.

43. A stentless heart valve bioprosthesis according to claim 36 formed entirely of biological tissue that is cryopreservable.

44. A stentless heart valve bioprosthesis according to claim 36 wherein the biological tissue thereof is preserved by chemical fixation.

45. A stentless heart valve bioprosthesis according to claim 36 wherein the sewing ring further comprises a quantity of material that is captured between the subvalvular lip and said sewing ring tissue.

46. A stentless heart valve bioprosthesis according to claim 45 wherein the material captured between the subvalvular lip and said sewing ring tissue is sized and located to impart a desired shape to said sewing ring.

47. A stentless heart valve prosthesis according to claim 36 formed entirely of cryopreservable material.

48. A stentless heart valve prosthesis according to claim 47 which has been cryopreserved.

49. A stentless heart valve prosthesis according to claim 48 wherein the bioprosthesis is a heterograft formed of tissue harvested from a non-human species.

50. A stentless heart valve prosthesis according to claim 49 wherein the animal from which the tissue is harvested was genetically engineered to produce tissue suitable for transplantation into a human recipient without substantial immunogenic rejection.

* * * * *